United States Patent [19]

Takami

[11] Patent Number: 4,483,585
[45] Date of Patent: Nov. 20, 1984

[54] ILLUMINATING DEVICE HAVING OPTICAL LIGHT GUIDE FORMED AS FIBRE BUNDLE

[75] Inventor: Akiyoshi Takami, Saitama, Japan

[73] Assignee: Olympus Optical Co., Ltd., Japan

[21] Appl. No.: 444,471

[22] Filed: Nov. 24, 1982

[30] Foreign Application Priority Data

Dec. 18, 1981 [JP] Japan ................................. 56-203637

[51] Int. Cl.³ .............................................. G02B 5/17
[52] U.S. Cl. ................................ 350/96.24; 350/96.18; 350/96.26
[58] Field of Search ............... 350/96.15, 96.18, 96.24, 350/96.25, 96.26, 168, 445

[56] References Cited

U.S. PATENT DOCUMENTS

3,926,501  12/1975  Hama ........................... 350/96.18
4,294,511  10/1981  Yamashita et al. ............. 350/96.18

*Primary Examiner*—John D. Lee
*Assistant Examiner*—Robert E. Wise
*Attorney, Agent, or Firm*—Ostrolenk, Faber, Gerb & Soffen

[57] ABSTRACT

An illuminating device including an optical light guide in the form of a fibre bundle, and a light source having a condenser lens to incident the incidence end surface of the fibre bundle is disclosed. An optical reflecting body having a peripheral reflecting portion is attached to the incidence end surface of the fibre bundle. Parameters of the lens and the optical reflecting body are determined to decrease light loss and to uniformly distribute light on the incidence end surface. The relation between the parameters is represented as formulae which in one case is applicable when the light intensity distribution of the bright spot image is peaked and in another case is applicable when the distribution is substantially flat.

32 Claims, 7 Drawing Figures

HEIGHT OF BRIGHT SPOT IMAGE

ILLUMINATING DEVICE HAVING OPTICAL LIGHT GUIDE FORMED AS FIBRE BUNDLE

BACKGROUND OF THE INVENTION

The present invention relates to an illuminating device having optical light guide in the form of a fibre bundle which may be used as an endoscope.

Generally, optical light guide fibres are made from glass or plastic material by crucible, acid melting method, rod, or thermal fusion method. These fibres are bundled, end rings are fitted at both ends of the bundle, and both ends are suitably ground to form a fibre bundle of flexible, semi-rigid or rigid conduit.

Such fibre bundles are used in light communication systems, illuminating devices sensor heads, light image transportation systems, illuminating devices light and safety anti-explosion devices. In any case, it is important to obtain a low loss and good light transporting fibre bundle.

One proposal to achieve this result is described in Japanese Laid Open Patent Application No. 19761/1979. This application attempts to decrease Fresnel reflection on both input and output end surfaces of the fibre bundle. To this end, a reflection decreasing layer e.g. $MgF_2$ is applied on a glass base plate having substantially the same refractive index as that of the fibre bundle and the glass base plates are adhered on the input and output end surfaces of the fibre bundle by a transparent adhesive having substantially the same refractive index as that of the fibre bundle.

While this structure decreases Fresnel reflection loss on both the end surfaces of the fibre bundle, it does not uniformly distribute input light to the input surface of the fibre bundle.

In the field of endoscopy, high accuracy and high capacity are desired and especially a high level of light transmission is desired. In conventional endoscopes, to improve light transmission, a strong light source, e.g. small xenon lamp of high luminance, is used and also a condenser lens is inserted to concentrate the high output of the lamp in narrow end surface of the fibre bundle efficiently.

However, this structure may cause other problems such as a shortened life of the lamp and a burning of the end surface of the fibre bundle by highly concentrated high luminance light. Consequently, the most intimate problem of such illuminating device is to concentrate the illuminating light from the light source uniformly and with least light loss to the incidence end surface of the fibre bundle.

SUMMARY OF THE INVENTION

Accordingly, the primary object of the present invention is to provide an illuminating device having an optical light guide formed as a fibre bundle in which illuminating light from light source is distributed substantially uninformly to the entire incidence end surface of the fibre bundle.

Another object of the present invention is to provide an illuminating device having optical light guide in the form of a fibre bundle in which illuminating light from the light source is applied substantially uniformly and with the least light loss to substantially the entire incidence end surface of the fibre bundle.

The illuminating device having the fibre bundle according to the present invention comprises an optical reflecting body having a peripheral reflecting surface attached to the incidence end surface of the fibre bundle. Parameters, i.e. radius, length and refractive index of the optical reflecting body, effective radius of the fibre bundle, air equivalent length between the bright spot image of illuminating light and incidence end surface of the optical reflecting body, height of the upper ray on the incidence end surface of the optical reflecting body, height and angle to the optical axis of the marginal ray are determined in relation to specific formulae. The illuminating device according to the present invention distributes illuminating light from the light source substantially uniformly to substantially the entire incidence end surface of fibre bundle with the least light loss. Thus, light transmission efficiency is improved and too narrow a concentration of light on the incidence end surface of the fibre bundle is avoided.

The objects and advantages of the invention will become apparent as the following detailed description with reference to the accompanying drawing given by way of example, in which:

EXPLANATION OF PRIOR ART

Before explaining the embodiments of the present invention, a conventional illuminating device utilizing an optical light guide formed as fibre bundle will be explained referring to FIG. 1.

Figure 1:
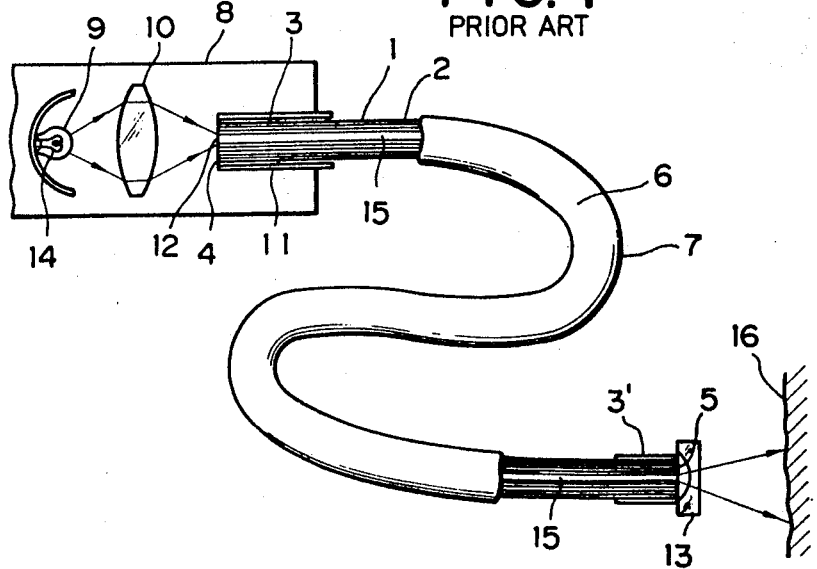
FIG. 1 is a schematic side view of a conventional illuminating device utilizing fibre bundle.

In FIG. 1, 1 designates a fibre bundle formed of a bundle of glass fibres 2 of e.g. tens to thousands of fibres. Rings 3 and 3' are fitted at opposite ends of the bundle, and a thermo-setting resin is adhered between the fibres and also between the rings 3 and 3' and the bundle 2. The incidence end surface 4 and emerging end surface 5 of the fibre bundle 2 are ground flat. The flexible portion 6, located between the both ends 4 and 5 of the bundle 2, is covered by a cover tube 7 of e.g. silicone.

A light source device 8 comprises a special lamp 9 e.g. halogen lamp or xenon lamp, a condenser lens 10 and a connector 11. When the lamp 9 is lighted, bright spot image 12 produced by the lens 10 is formed on the incidence end surface 4 of the fibre bundle 1 to perform effective incidence of illuminating light from the light source. On the emerging end surface 5 of the fibre bundle 1, an illuminating lens 13 is mounted to diverge illuminating light which is transmitted through the bundle of glass fibres 2.

In the above-described illuminating device utilizing optical light guide formed as fibre bundle, the incidence end surface 4 of the fibre bundle 1 is inserted into the connector 11 of the light source device 8, and the lamp 9 is lighted so that the bright spot image 12 (located at the focal point of lens 10) of the filament 14 of the lamp 9 is formed on the incidence end surface 4 of the fibre bundle 1. When the dimension of the bright spot image 12 of the filament 14 is smaller than the effective diameter ($\phi$D) of the incidence end surface 4 of the fibre bundle 1, a portion of the incidence end surface 4 is illuminated stronger than other portions. The fibre bundle 1 for illuminating purpose, arrangement of each fibre at the incidence end surface 4 and the emerging end surface 5 does not perfectly correspond compared with image transporting fibre bundle. However, fibres tend to gather to form multi-fibres 15 shown in FIG. 1, so that correspondence between the incidence end surface and the emerging end surface can not be denied. Thus, in generally speaking, the arrangement of each fibre at the incidence end surface 4 and the emerging end surface 5 corresponds with each other evenly for illuminating purposes. Thus, when the bright spot image 12 of the light source 9 is formed on a portion of the incidence end surface 4 of the fibre bundle 1, e.g. on the multi-fibres 15, the bright spot image 12 is also formed on the emerging end surface 5 without scattering in wide range. The illuminating light from the end surface 5 is diverged within narrow range of a body 16 to be observed. Such illuminating light distribution is undesirable when observing a body cavity using an endoscope.

Figure 2:
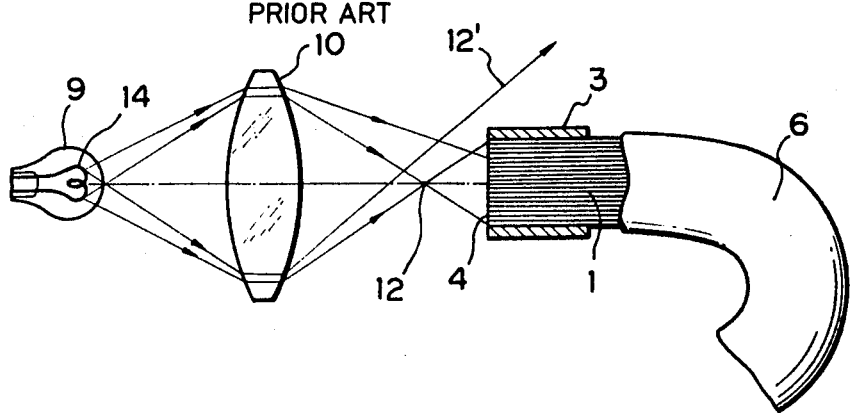
FIG. 2 is a schematic side view of a portion of another conventional illuminating device with schematic beam path.

To overcome this problem, the incidence end surface of the fibre bundle 1 is separated a few millimeter from the imaging point of the bright spot image 12 as shown in FIG. 2. Thus, bright spot image on the incidence end surface 4 fades to distribute illuminating light all through the end surface 4. However, as the bright spot is not a sharp spot, light 12' on the periphery of the bright spot illuminates out of the incidence end surface 4 of the fibre bundle 1. Thus, uneven distribution at incidence end point is avoided, however, the amount of light utilized is decreased and light transport efficiency is decreased.

DETAILED DESCRIPTION OF THE EMBODIMENTS

In all the drawings the same reference numeral shows the same or similar part or portion for the sake of clarity.

Figure 3:
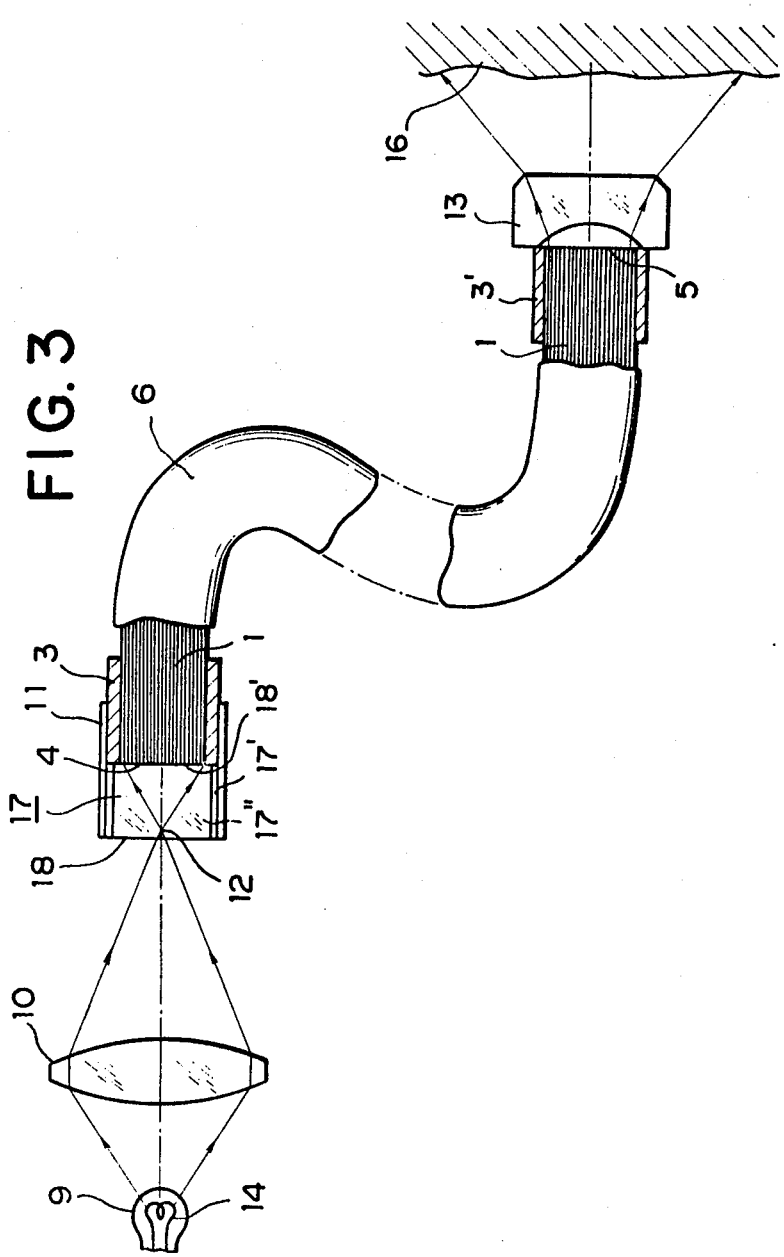
FIG. 3 is a schematic side view of an illuminating device, according to the present invention.

A first embodiment to explain basic construction of the present invention is shown in FIG. 3. A single light guide 17 is made of a core 17" and a clad 17' which is secured with outside surface of the core 17". The single light guide 17 acts as an optical reflecting body and is mounted in front of the incidence end surface 4 of the fibre bundle 1. When the single light guide 17 is connected with the fibre bundle 1, the bright spot image 12 of the light source 9 focuses in the single light guide 17 and diverges and then incidents into the end surface 4 of the fibre 1. Thus, peripheral light of the bright spot also incidents onto the end surface 4 of the fibre bundle 1 after being reflected off the peripheral wall surface of the single light guide 17.

By connecting the single light guide 17 on the incidence end surface 4 of the fibre bundle 1, illuminating light from the light source 9 can be applied to the incidence end surface 4 without light loss. However, to improve light transport efficiency, the dimension and refractive index of the single light guide 17 and imaging point of the bright spot image or air equivalent length of the imaging point from the incidence end surface 18 of the single light guide 17, must be accurately selected and determined.

The selection of the parameters of the single light guide 17 will be explained. In this case, the set condition is different when the light intensity distribution of the bright spot image 12 has high peak value or when the distribution is relatively uniform. Thus, each case must be considered separately.

Figure 4:
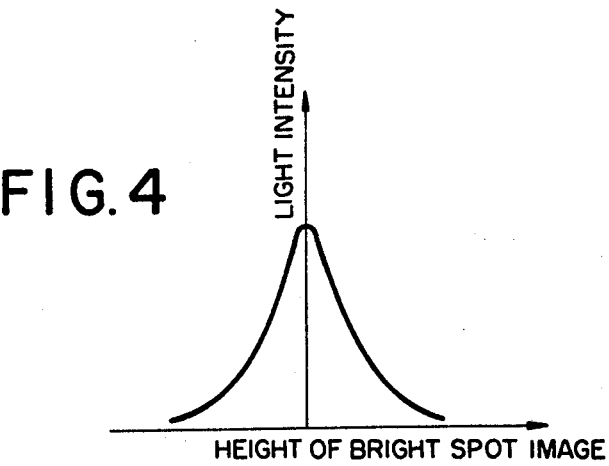
FIG. 4 is a diagram of light intensity distribution of bright spot image having peak value.

First, it will be assumed that the light intensity distribution of the bright spot image 12 of the light source has high peak value as shown in FIG. 4.

In a fibre bundle connecting with a single light guide 17, the parameters which must be examined to ensure that incident illuminating light will be uniformly distributed on the incidence end surface without causing light quantity loss are defined as follows:

d: axial length of the single light guide 17,
r̄: radius of the core 17" of the light guide 17,
n: refractive index of the core 17",
r: effective radius of the fibre bundle 1,
l: height of the bright spot image,
S: equivalent air length from the incidence end surface of the single light guide to the bright spot image, and is plus in the direction from the end surface 18 to the fibre bundle,
h: height of upper light at the incidence end surface of the single light guide 17,
k: height of marginal ray 19,
$\alpha$: angle of marginal ray 19 to optical axis,
C: radius of diverged bright spot on the incidence end surface of the fibre bundle.

At first, the randomness of the fibre bundle 1 is considered. The radius C of the diverged bright spot on the incidence end surface 4 of the fibre bundle 1 can be used practically when the radius C is more than $\frac{1}{3}$ of the effective radius r of the fibre bundle 1. Thus, the condition to incident illuminating light on the incidence end surface 4 of the fibre bundle 1 substantially uniformly without causing uneven distribution of light is:

$$C \geq \tfrac{1}{3} r \qquad (1)$$

As, $$C = (-S + d/n) \tan \alpha \qquad (2)$$

From formulae (1) and (2), $$(-S + d/n) \tan \alpha \geq \tfrac{1}{3} r \qquad (3)$$

The formula (3) describes the condition which is necessary to cause incident illuminating light to be substantially uniformly distributed on the incidence end surface of the fibre bundle 1.

Figure 5:
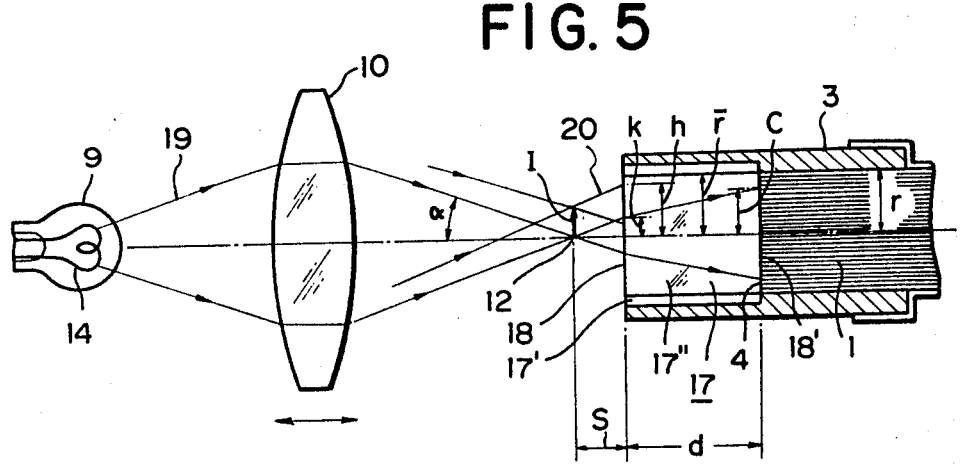
FIG. 5 is an enlarged front portion of FIG. 3 and shows beam path corresponding to light intensity distribution of bright spot image shown in FIG. 4.

To avoid light quantity loss on the incidence end surface 18 of the single light guide 17, upper side ray 20 shown in FIG. 5 must be incident in the single light guide 17. Thus:

$$h < \bar{r} \qquad (4)$$

As a practical matter, the outer portion of the divergence of the bright spot is rather dark, so that the formula (4) may be rewritten as:

$$(h + k)/2 < \bar{r} \qquad (5)$$

Accordingly, when parameters S, d, n and α are selected to satisfy formula (3), an illuminating device utilizing a fibre bundle is obtained which causes incident illuminating light to be substantially uniformly distributed on the incidence end surface of the fibre bundle. Also, when parameters S, d, n, α, h, k and $\bar{r}$ are selected to satisfy formulae (3) and (5), an illuminating device utilizing a fibre bundle is obtained which causes incident illuminating light to be substantially uniformly distributed on the incidence end surface 4 of the fibre bundle 1 without causing light loss.

Figure 6:
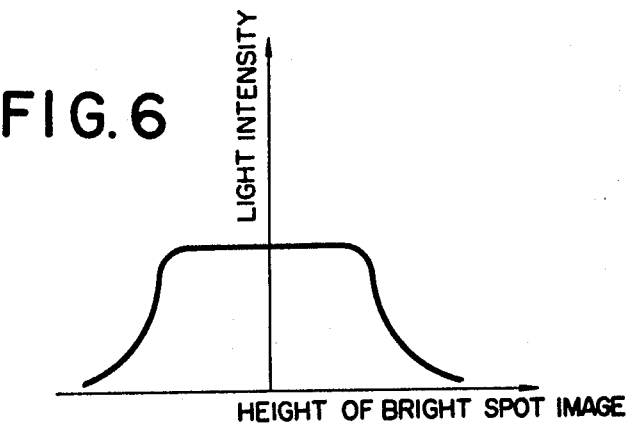
FIG. 6 is a diagram of light intensity distribution of bright spot image which is substantially flat.

Next, it is assumed that the light intensity distribution of the bright spot image 12 is substantially uniform as shown in FIG. 6.

Figure 7:
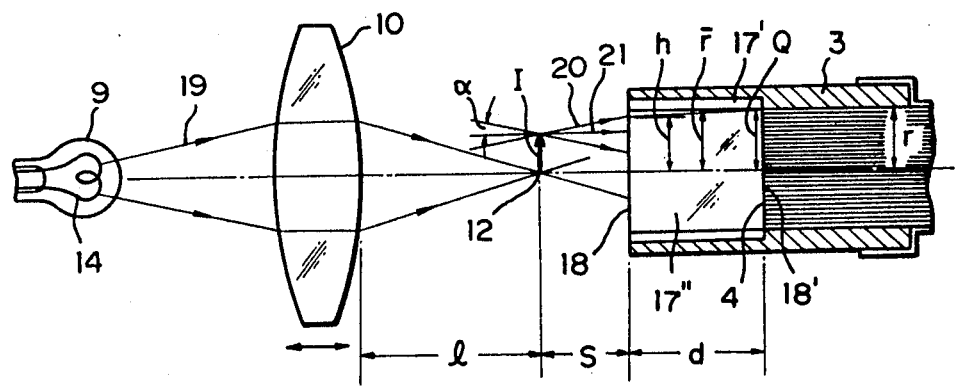
FIG. 7 is an enlarged front portion of FIG. 3 and shows beam path corresponding to light intensity distribution of bright spot image shown in FIG. 6.

In this case, the light transport path is shown in FIG. 7. Generally, the height I of the bright spot image is small compared with distance l between the light source lens 10 and the imaging point of the bright spot image 12, it can be considered that the principal ray 21 is substantially parallel to the optical axis. In this case, light stop is considered as lens frame. Now, the height of the upper ray 20 on the incidence end surface 4 of the fibre bundle 1 is represented as Q. To improve illumination light distribution on the incidence end surface 4, regarding the randomness of the fibre bundle 1, practically Q may be wider than ½ of effective radius r of the fibre bundle 1. Thus, $$Q \geq \tfrac{1}{2} r \tag{6}$$

As, $$Q = I + (-S + d/n) \tan \alpha \tag{7}$$

From the formulae (6) and (7), the condition which must be obtained to improve the illumination light distribution on the incidence end surface is:

$$I + (-S + d/n) \tan \alpha \geq \tfrac{1}{2} r \tag{8}$$

The condition to avoid light loss on the incidence end surface 18 of the single light guide 17 is that the upper ray 20 is within the single light guide 17. Thus, as in the first case, the light intensity distribution of the bright spot image has peak value, $$h < \bar{r} \tag{9}$$

Accordingly, in the second case where the light intensity distribution of the bright spot image is substantially uniform as shown in FIG. 6, when parameters I, S, d, n and α relating to the dimension of the single light guide 17 and imaging point of the bright spot image, are selected to satisfy the formula (8), the illuminating device utilizing a fibre bundle causes incident illuminating light to be substantially uniformly distributed on the incidence end surface of the fibre bundle. Also, when the parameters I, S, d, n, α, h and $\bar{r}$ are selected to satisfy formulae (8) and (9), the illuminating device utilizing a fibre bundle connected with the single light guide causes the incident illuminating light to be substantially uniformly distributed on the incidence end surface of the fibre bundle without causing light loss.

When light flux is not symmetrical with the optical axis, for example, when a light stop is used, the values of h, k and α in the equations (2), (3), (4), (5), (7) and (8) should adopt minimum values respectively.

The radius $\bar{r}$ of the core 17″ of the single light guide 17 may preferably be determined from the manufacturing stand point such that the core radius $\bar{r}$ of the single light guide 17 is larger than the effective radius r of the fibre bundle 1, so as to absorb misalignment between the single light guide 17 and the incidence end surface 4 of the fibre bundle 1. Thus, effective area of the fibre bundle 1 can be fully utilized to transport illuminating light.

The numerical aperture of the single light guide 17 may preferably be the same or greater than that of the fiber bundle 1 so that the maximum angular component of light can be transported on the incidence end surface 4 of the fibre bundle 1.

In an illuminating device a utilizing light transporting fibre bundle 1, the single light guide 17 is connected with the incidence end surface 4 of the fibre bundle 1, and various parameters of the construction parts can be determined by the above described formulae according to the present invention. In practice, construction parts can be easily made corresponding to the above-mentioned formulae. However, in assembly, when the fiber bundle 1 is connected with the connector 11 of the light source device 8, some misalignment can occur. To absorb the misalignment, the condenser lens 10 of the light source device 8 is axially adjustable to adjust the imaging point and size of the bright spot image. Thus, some parameters can be adjusted. Consequently, illuminating light will be incident on the incidence end surface 4 of the fibre bundle 1 most efficiently with minimum loss and over the full effective area of the end surface.

In the above-mentioned illuminating device, when Fresnel reflection loss is decreased, light transport characteristics is improved. To decrease the Fresnel reflection loss, both end surfaces 18 and 18′ of the single light guide 17 and the incidence end surface 4 of the fibre bundle 1 are coated with thin layer of material having a similar or the same refractive index with that of the core 17″ of the single light guide 17, e.g. magnesium fluoride or silicon oxide. The adhesive between the incidence end surface 4 of the fibre bundle 1 and the single light guide 17 may also be formed of a material having similar or same refractive index with that of the core 17″ of the single light guide 17. Such material may preferably be a thermosetting resin or organic silicone compound of transparent, relatively high heat resistivity, and slightly less hardness than the core when cured. Such coating of thin layer and applying adhesive decrease end surface reflection loss and also act to water proof the end surfaces.

In the above-mentioned embodiment, the light reflection body which is connected with the incidence end surface 4 of the fibre bundle 1 is a cladded single light guide 17. However, a cylindrical reflection body or a conical reflection body which reflects incidence light at peripheral wall surface may be used in place of the single light guide 17. Off course, the optical reflecting body 17 may preferably made from transparent material to assure good transmission factor.

What is claimed is:

1. An illuminating device utilizing an optical light guide in the form of a fibre bundle, said illuminating device comprising a light source, an optical light guide in the form of a fibre bundle, an optical reflecting body having a peripheral reflecting portion and attached to the incidence end surface of the fibre bundle, and a light source lens guiding illuminating light from the light source to the fibre bundle; said lens and said optical reflecting body having such a structure that when the bright spot image of the light source formed by the lens has a peaked light intensity distribution, the following condition is satisfied:

$$(-S + d/n) \tan \alpha \geq \tfrac{1}{2} r$$

in which:
S is the air equivalent length between the bright spot image and the incidence end surface of the optical reflecting body which is plus from the end surface to the fibre bundle,
d is the length of the optical reflecting body,
n is the refractive index of the optical reflecting body,
α is the angle of marginal ray relative to optical axis, and
r is the effective radius of the fibre bundle.

2. An illuminating device according to claim 1, in which said light source lens is mounted for axial displacement relative to the light source to regulate the location of the bright spot image.

3. An illuminating device according to claim 1, in which the numerical aperture of the optical reflecting body is the same or greater than that of said fibre bundle.

4. An illuminating device according to claim 1, in which the diameter of the optical reflecting body is greater than that of the effective diameter of said fibre bundle.

5. An illuminating device according to claim 1, in which said optical reflecting body is made of transparent optical material.

6. An illuminating device according to claim 1, in which said optical reflecting body and said fibre bundle are adhered by an adhesive having the same or similar refractive index as that of said optical reflecting body.

7. An illuminating device according to claim 1, in which both end surfaces of the optical reflecting body and the incident end surface of the fibre bundle are coated with a reflection decreasing layer having the same or similar refractive index as that of the optical reflecting body.

8. An illuminating device according to claim 1, in which both end surfaces of the optical reflecting body and the incident end surface of the fibre bundle are coated with a reflection decreasing layer having the same or similar refractive index as that of the optical reflecting body, and said optical reflecting body and said fibre bundle are adhered by an adhesive having the same or similar refractive index as that of said optical reflecting body.

9. An illuminating device utilizing an optical light guide in the form of a fibre bundle, said illuminating device comprising a light source, an optical light guide in the form of a fibre bundle, an optical reflecting body having a peripheral reflecting portion and being attached to the incidence end surface of the fibre bundle, and a light source lens guiding illuminating light from the light source to the fibre bundle; said lens and said optical reflecting body having such a structure that when the bright spot image of the light source formed by the lens has a peaked light intensity distribution, the following conditions are satisfied:

$$(-S + d/n) \tan \alpha \geq \tfrac{1}{2} r$$

and $$(h+k)/2 < \bar{r}$$

in which:
S is the air equivalent length between the bright spot image and the incidence end surface of the optical reflecting body which is plus from the end surface to the fibre bundle,
d is the length of the optical reflecting body,
n is the refractive index of the optical reflecting body,
α is the angle of marginal ray relative to the optical axis,
r is the effective radius of the fibre bundle,
h is the height of upper ray on incidence end surface of the optical reflecting body,
k is the height of marginal ray,
$\bar{r}$ is the radius of the optical reflecting body.

10. An illuminating device according to claim 9, in which said light source lens is axially displacably mounted relative to the light source to regulate the location of the bright spot image.

11. An illuminating device according to claim 9, in which the numerical aperture of the optical reflecting body is the same or greater than that of said fibre bundle.

12. An illuminating device according to claim 9, in which the diameter of the optical reflecting body is greater than that of the effective diameter of said fibre bundle.

13. An illuminating device according to claim 9, in which said optical reflecting body is made of transparent optical material.

14. An illuminating device according to claim 9, in which said optical reflecting body and said fibre bundle are adhered by an adhesive having the same or similar refractive index as that of said optical reflecting body.

15. An illuminating device according to claim 9, in which both end surfaces of the optical reflecting body and the incident end surface of the fibre bundle are coated with a reflection decreasing layer having the same or similar refractive index as that of the optical reflecting body.

16. An illuminating device according to claim 9, in which both end surfaces of the optical reflecting body and the incident end surface of the fibre bundle are coated with a reflection decreasing layer having the same or similar refractive index as that of the optical reflecting body, and said optical reflecting body and said fibre bundle are adhered by an adhesive having the same or similar refractive index as that of said optical reflecting body.

17. An illuminating device utilizing an optical light guide in the form of a fibre bundle, said illuminating device comprising a light source, an optical light guide in the form of a fibre bundle, an optical reflecting body having a peripheral reflecting portion and attached to the incidence end surface of the fibre bundle, and a light source lens guiding illuminating light from the light source to the fibre bundle; said lens and said optical reflecting body being so structured that when the light intensity distribution of the bright spot image of the light source formed by the lens is substantially flat, the following condition is satisifed:

$$l + (-S + d/n) \tan \alpha \geq \tfrac{1}{2} r$$

in which:
l is the height of the bright spot image,
S is the air equivalent length between the bright image spot and the incidence end surface of the optical reflecting body which is plus from the end surface to the fibre bundle,
d is the length of the optical reflecting body,
n is the refractive index of the optical reflecting body,
α is the angle of marginal ray relative to the optical axis,
r is the effective radius of the fibre bundle.

18. An illuminating device according to claim 17, in which said light source lens is axially displacably mounted relative to the light source to regulate the location of the bright spot image.

19. An illuminating device according to claim 17, in which the numerical aperture of the optical reflecting body is the same or greater than that of said fibre bundle.

20. An illuminating device according to claim 17, in which the diameter of the optical reflecting body is greater than that of the effective diameter of said fibre bundle.

21. An illuminating device according to claim 17, in which said optical reflecting body is made of transparent optical material.

22. An illuminating device according to claim 17, in which said optical reflecting body and said fibre bundle are adhered by an adhesive having the same or similar refractive index as that of said optical reflecting body.

23. An illuminating device according to claim 17, in which both end surfaces of the optical reflecting body and the incident end surface of the fibre bundle are coated with a reflection decreasing layer having the same or similar refractive index as that of the optical reflecting body.

24. An illuminating device according to claim 17, in which both end surfaces of the optical reflecting body and the incident end surface of the fibre bundle are coated with a reflection decreasing layer having the same or similar refractive index as that of the optical reflecting body, and said optical reflecting body and said fibre bundle are adhered by an adhesive having the same or similar refractive index as that of said optical reflecting body.

25. An illuminating device utilizing an optical light guide in the form of a fibre bundle, said illuminating device comprising a light source, an optical light guide in the form of a fibre bundle, an optical reflecting body having a peripheral reflecting portion and attached to the incidence end surface of the fibre bundle, and a light source lens guiding illuminating light from the light source to the fibre bundle; said lens and said optical reflecting body being so structured that when the light intensity distribution of the bright spot image of the light source formed by the lens is substantially flat, the following conditions are satisfied:

$$I + (-S + d/n) \tan \alpha \geq \tfrac{1}{2} r$$

and $$h < \bar{r}$$

in which:
I is the height of the bright spot image,
S is the air equivalent length between the bright spot image, and the incidence end surface of the optical reflecting body which is plus from the end surface to the fibre bundle,
d is the length of the optical reflecting body,
n is the refractive index of the optical reflecting body,
α is the angle of marginal ray relative to the optical axis,
r is the effective radius of the fibre bundle,
h is the height of upper ray on incidence end surface of the optical reflecting body,
$\bar{r}$ is the radius of the optical reflecting body.

26. An illuminating device according to claim 25, in which said light source lens is axially displacably mounted relative to the light source to regulate the location of the bright spot image.

27. An illuminating device according to claim 25, in which the numerical aperture of the optical reflecting body is the same or greater than that of said fibre bundle.

28. An illuminating device according to claim 25, in which the diameter of the optical reflecting body is greater than that of the effective diameter of said fibre bundle.

29. An illuminating device according to claim 25, in which said optical reflecting body is made of transparent optical material.

30. An illuminating device according to claim 25, in which said optical reflecting body and said fibre bundle are adhered by an adhesive having the same or similar refractive index as that of said optical reflecting body.

31. An illuminating device according to claim 25, in which both end surfaces of the optical reflecting body and the incident end surface of the fibre bundle are coated with a reflection decreasing layer having the same or similar refractive index as that of the optical reflecting body.

32. An illuminating device according to claim 25, in which both end surfaces of the optical reflecting body and the incident end surface of the fibre bundle are coated with a reflection decreasing layer having the same or similar refractive index as that of the optical reflecting body, and said optical reflecting body and said fibre bundle are adhered by an adhesive having the same or similar refractive index as that of said optical reflecting body.

* * * * *